United States Patent [19]
Janda et al.

[11] Patent Number: 5,559,000
[45] Date of Patent: Sep. 24, 1996

[54] ENCODED REACTION CASSETTE

[75] Inventors: Kim D. Janda, San Diego; Richard A. Lerner, La Jolla; Hicham Fenniri, San Diego, all of Calif.

[73] Assignee: The Scripps Research Institute, La Jolla, Calif.

[21] Appl. No.: 374,050

[22] Filed: Jan. 18, 1995

[51] Int. Cl.⁶ .............................. C12Q 1/68; C12Q 1/70; C12P 19/31; G01N 27/26
[52] U.S. Cl. .................. 435/6; 435/7.1; 435/7.6; 435/91.2; 435/5; 536/24.3; 530/388.1
[58] Field of Search ................... 435/6, 7.1–7.9, 435/91.2; 536/24.3–.33; 530/388.1

[56] References Cited

U.S. PATENT DOCUMENTS 4,272,506  6/1981  Schwarzenberg ..................... 424/8
5,190,864  3/1993  Giese et al. ........................... 435/41
5,318,897  6/1994  Paul ................................... 435/68.1
5,380,833  1/1995  Urdea ................................ 536/22.1
5,410,068  4/1995  Coull et al. .......................... 548/545
5,432,062  7/1995  Turacek ............................. 435/68.1

*Primary Examiner*—W. Gary Jones
*Assistant Examiner*—Dianne Rees
*Attorney, Agent, or Firm*—Donald G. Lewis

[57] ABSTRACT

A reaction cassette has been designed for the highly sensitive detection of the making and breaking of chemical bonds. The system may be employed as a companion device to be used in the search for antibody and other novel catalysts. The cassette also has important clinical applications in the design of diagnostic reagents. In its fully encoded format this methodology is capable of both detecting and decoding chemical events.

13 Claims, 3 Drawing Sheets

ENCODED REACTION CASSETTE

STATEMENT OF GOVERNMENT RIGHTS

This invention was made, in part, with government support under Grant No.'s GM 48351 from the National Institutes of Health. The U.S. government may have certain rights in the invention.

FIELD OF INVENTION

The invention relates to methods and reagents for assaying cleavage and ligation reactions and the activity of catalytic molecules which promote cleavage and ligation reactions. More particularly, the invention relates to assays which employ substrates covalently linked both to a solid phase matrix and to a nucleotide strand encoded to identify the substrate and including polymerization chain reaction (PCR) primer sequences for amplifying such encoded sequences.

BACKGROUND OF THE INVENTION

Cleavage and ligation reactions can be assayed by monitoring either the appearance of reaction products or the disappearance of substrates. For example, protein or peptide proteolysis can be monitored by following the appearance of cleavage products. Cleavage products may be separated from substrate by gel electrophoresis or by chromatographic separation and monitored by UV absorption or colorimetric assay. Similarly, polynucleotide ligation can be monitored by following the appearance of ligation products.

If the cleavage or ligation activity is low, the detection signal may require amplification to detect the reaction products. For example, radio labeled substrates may be synthesized and the resulting reaction products may be detected by radio immunoassay. Alternatively, if the substrate is conjugated to an enzyme which catalyzes a colorimetric reaction, the resultant reaction products may be detected by means of an enzyme immunoassay. Highly sensitive enzyme immunoassays have been developed. When employed at their limit of sensitivity, the signal produced by an enzyme immunoassay in response to the presence of reaction product becomes comparable to the background signal.

In the catalytic antibody field, antibody libraries are routinely screened in order to identify catalytically active antibody. There are two limitations to creating a useful catalytic antibody, viz.: 1.) designing a productive immunogen which is an analog of the substrate or reaction intermediate and producing an antibody library therewith; and 2.) screening the resultant antibody library for the desired catalytic activity. In short, the limitations are display and detection. The problem of display can be facilitated by converting the antibody diversity into a combinatorial library in phage where the recognition and replication functions are linked in a single entity and monitored by simple binding events. However, the screening of phage particles which display only a small number of catalytic antibody molecules requires a highly sensitive assay methodology. In such instances, the displayed catalytic activity may be only slightly higher than background activity. Prior art methods for assaying cleavage and ligation reactions sometimes lack the requisite sensitivity for identifying small quantities of low activity antibody. In some instances, catalytic antibody having a low level of catalytic activity can be useful if it is the only antibody identified to have such catalytic activity and/or if it is employed in an "evolutionary scheme" for generating antibodies having higher levels of catalytic activity. Accordingly, the sensitivity of the assay employed for screening an antibody library, may be the limiting factor with respect to the identification of useful antibody. The ease or difficulty of the assay may also limit the willingness of workers to perform these assays.

In instances in which one can obtain antibodies to the reaction product or substrate, an immuno-PCR assay may be constructed and employed as a detection system. (T. Sano et al., *Science* (1992): vol. 258, pages 120–122). An immuno-PCR assay is similar to an enzyme immunoassay except that the enzyme-antibody conjugate is replaced by an antibody conjugated to a PCR amplifiable polynucleotide strand. Immuno-PCR assays are highly sensitive. However, at very low levels of antigen, the immuno-PCR assay is limited by non-specific binding of the antibody-polynucleotide conjugate.

What is needed is a highly sensitive assay for detecting cleavage or ligation reactions. The assay should not employ an antibody conjugate and should have the lowest possible background signal. The assay should be labor efficient and should be adaptable for assaying any cleavage or ligation reaction.

SUMMARY OF THE INVENTION

The invention is directed to an encoded reaction cassette employable for detecting cleavage or ligation reactions and to assays employing such cassettes. Cassettes may be constructed for assaying any cleavage or ligation reaction.

A reaction cassette is designed for the highly sensitive detection of the making and breaking of chemical bonds. The system may be employed as a companion device to be used in the search for antibody and other novel catalysts. The cassette may also have important clinical applications in the design of diagnostic reagents. In its fully encoded format this methodology is capable of both detecting and decoding chemical events.

The assay of the present application was originally developed for application in the field of antibody catalysis. However, it may also be employed for assaying any synthetic or enzymatic reaction, including those important to diagnostic assays in medicine. When one is using the cassette to search for a single reaction, only one DNA sequence is necessary. However, in a fully encoded format, one can test multiple substrates simultaneously by using unique polynucleotide sequences for each substrate. The nature of the reaction that occurred may be simply determined by the sequence of the polynucleotide either after the PCR reaction or upon cloning of the polynucleotide according to the method of A. D. Mirzabekov (*TIBTECH* (1994): vol. 12, pages 27–32). In essence, one can create an encoded combinatorial library of substrates to learn about reaction specificities. One can design systems in which a combinatorial library of catalysts is screened against a combinatorial library of substrates to find new catalysts and refine their substrate specificity in a single operation. Finally, the disclosed method for constructing encoded cassettes may be adapted to an operating procedure in which a substrate cassette is built as a companion to any experiment where one is searching for a new catalyst. This enables the researcher or investigator to design experiments which are independent of whether the reaction products can be easily assayed by prior art methods. Thus, each time one contemplates searching for an enzyme the first step is to construct an encoded reaction cassette to detect reactivity.

More particularly, the invention is directed to an encoded reaction cassette for assaying a cleavage reaction. The reaction cassette includes a substrate covalently linked to a solid phase matrix, wherein the substrate is of a type which is suspectable to cleavage by means of the cleavage reaction. Linked to the substrate is a first polynucleotide which includes a first PCR primer sequence, an encoding sequence, and a second PCR primer sequence. The encoding sequence is positioned between the first and second PCR sequences. In a preferred embodiment, the encoded reaction cassette may also include a first and second linker. The first linker covalently links the solid phase matrix to the substrate. The second linker covalently links the substrate to the first polynucleotide. Peptides are preferred substrates. However, any cleavable substrate may be employed. In an alternative embodiment the encoded reaction cassette may include one or more additional polynucleotides linked to the substrate for further amplifying the signal. These additional polynucleotides also include the same first PCR primer sequence, encoding sequence, and second PCR primer sequence and may be linked to the substrate via additional linkers.

The invention is also directed to an admixture of cleavage products from an encoded reaction cassette which has been exposed to a cleavage agent. This admixture includes a solid phase cleavage product and a soluble phase cleavage product. The solid phase cleavage product includes a first cleavage product of a substrate covalently linked to the solid phase matrix. The soluble phase cleavage product includes a second cleavage product of the substrate covalently linked to the first polynucleotide.

The invention is also directed to a method for detecting a cleavage agent within a sample. The method comprises the following steps. In the first step, the sample is admixed with an encoded reaction cassette under reaction conditions for promoting cleavage of the substrate to produce a cleavage products. If the sample has cleavage activity, cleavage products will be generated, i.e., a solid phase cleavage product and a soluble phase cleavage product. In the second step, soluble phase cleavage product is separated and isolated from the solid phase cleavage products and from uncleaved encoded reaction cassettes. In the third step, the encoding sequence of the polynucleotide of the soluble phase cleavage product isolated in the second step is amplified by means of a polymerization chain reaction (PCR). In the fourth step, the amplified encoding sequence amplified is detected. And, in an alternative fifth step, the signal obtained in the fourth step is correlated with known substrates and/or cleaving agents to obtain quantitative results.

Another aspect of the invention is directed to an admixture of unligated reactants for producing an encoded ligation cassette for assaying a ligation reaction. The admixture may include a solid phase ligation component and a soluble phase ligation component. The solid phase ligation component includes a first ligation reactant covalently linked to a solid phase matrix. The soluble phase ligation component includes a second ligation reactant covalently linked to a first polynucleotide. As before, the first polynucleotide includes an encoding sequence positioned between a first PCR primer sequence and a second PCR primer sequence. The first and second ligation reactants are capable of ligation in the presence of a ligating agent to join the solid phase and soluble phase ligation components so as to form an encoded ligation cassette. In a preferred embodiment, the first and second ligation reactants are fragments of a ligatible oligonucleotide. However, any pair of ligatible molecules may be employed. The encoded ligation cassette is analogous to the encoded reaction cassette except that a ligation product separates the solid phase matrix from the first polynucleotide. However, unlike the encoded reaction cassette, the encoded ligation cassette need not be susceptible to cleavage by a cleavage agent. Preferred ligating agents have ligation activity with respect to the first and second ligation reactants. More particularly, a preferred ligation agent is polynucleotide ligase and preferred first and second ligation reactants are ligatible oligonucleotides.

The invention is also directed to a method for detecting a nucleotide ligating agent within a oligonucleotide sample. The method includes several steps. In the first step, the sample is combined with an admixture of ligation components. The resultant admixture is the incubated for producing an encoded ligation cassette. In the second step, the encoded ligation cassette formed above is then separated and isolated together with unligated portions of the solid phase ligation component from the unligated portion of the soluble phase ligation component. The encoding sequence of the polynucleotide of the encoded ligation cassette may then be amplified by means of PCR, detected, and correlated with the presence of the ligation agent. Polynucleotide ligase is a preferred ligation agent. In this instance, the ligation product included within the encoded ligation cassette is a polynucleotide susceptible to ligation by the ligase.

DETAILED DESCRIPTION

DESIGN FEATURES OF THE CASSETTE

The invention combines two prior art methods, viz.: 1. the technique of synthesizing polymers on solid support; and 2. the technique of PCR (Polymerase Chain Reaction). The overall approach is illustrated in FIG. 1.

Figure 1:
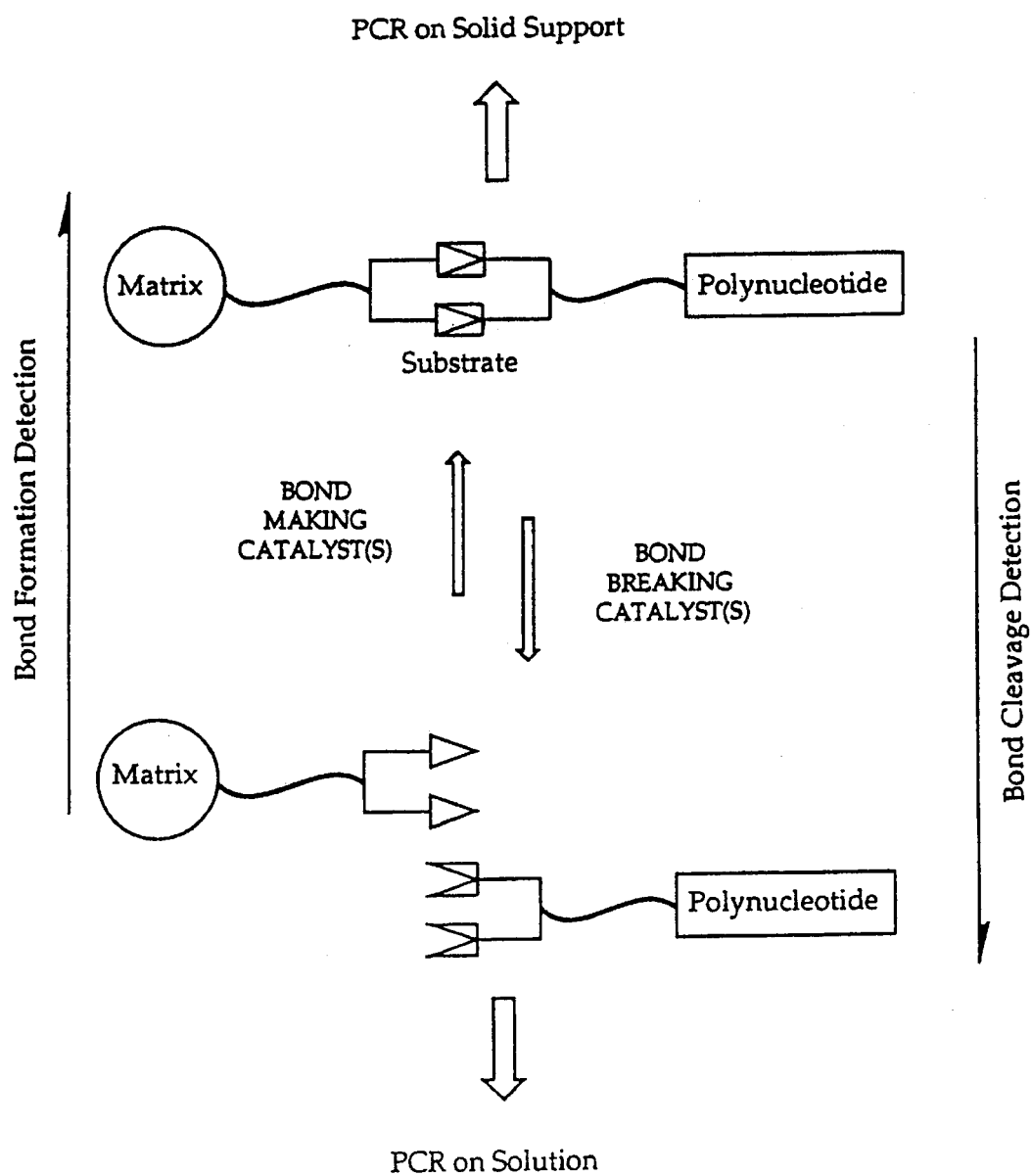
FIG. 1 is a schematic illustration of the general principle of the reaction cassette.

The central operative feature of the reaction cassette is the liberation (cleavage event) or capture (bond formation) of a polynucleotide containing two primers (FIG. 1). Thus, when an appropriately functionalized solid support (FIG. 1) is exposed to a catalyst or a library of catalysts that are able to selectively cleave the reaction cassette at the substrate juncture, single stranded DNA (polynucleotide) will be released and can be amplified by the PCR. Furthermore, the sequence of the polynucleotide may be chosen in such a way that it reflects the nature of the substrate, so that a library of encoded substrates can be designed. When substrate libraries such as these are exposed to a library of catalysts one can identify not only the catalyst but also the substrate since the sequence of the cleaved polynucleotide encodes and thus identifies which substrate sequence has been cleaved. In addition to the above methodology, our cassette reaction technique allows one to follow a bond formation event via the inverse pathway (FIG. 1). In this initial report we describe the application of our methodology to the study of enzyme catalyzed bond cleavage.

The Matrix. In attempting to implement this technology we encountered a variety of problems. First, certain matrix materials, like CPG (Controlled Pore Glass), were labile and liberated the polynucleotide-substrate hybrid leading to an undesired background reaction. We presumed that cleavage of a bond between the solid support and the first linker was responsible for this problem. In addition to the problem with its lability, CPG possesses free hydroxyl groups on which the polynucleotide chain can be grown during polynucleotide synthesis (25), leading to unwanted labile bonds. A second difficulty was that enzymatic cleavage of the cassette was slow and incomplete (data not shown) because of steric hindrance of the substrate by the matrix and/or the polynucleotide. For this reason we had to extend the length of the linkers either between the solid support and the substrate and/or the substrate and the polynucleotide. For our purposes TentaGel was found to have much better mechanical and chemical properties. Furthermore, it possesses a long polyoxyethylene arm which attenuates the hindrance problem. Finally, the synthesis had to be simple so that the cassette can be easily prepared in a short time. All these considerations led to the strategy depicted in scheme 1.

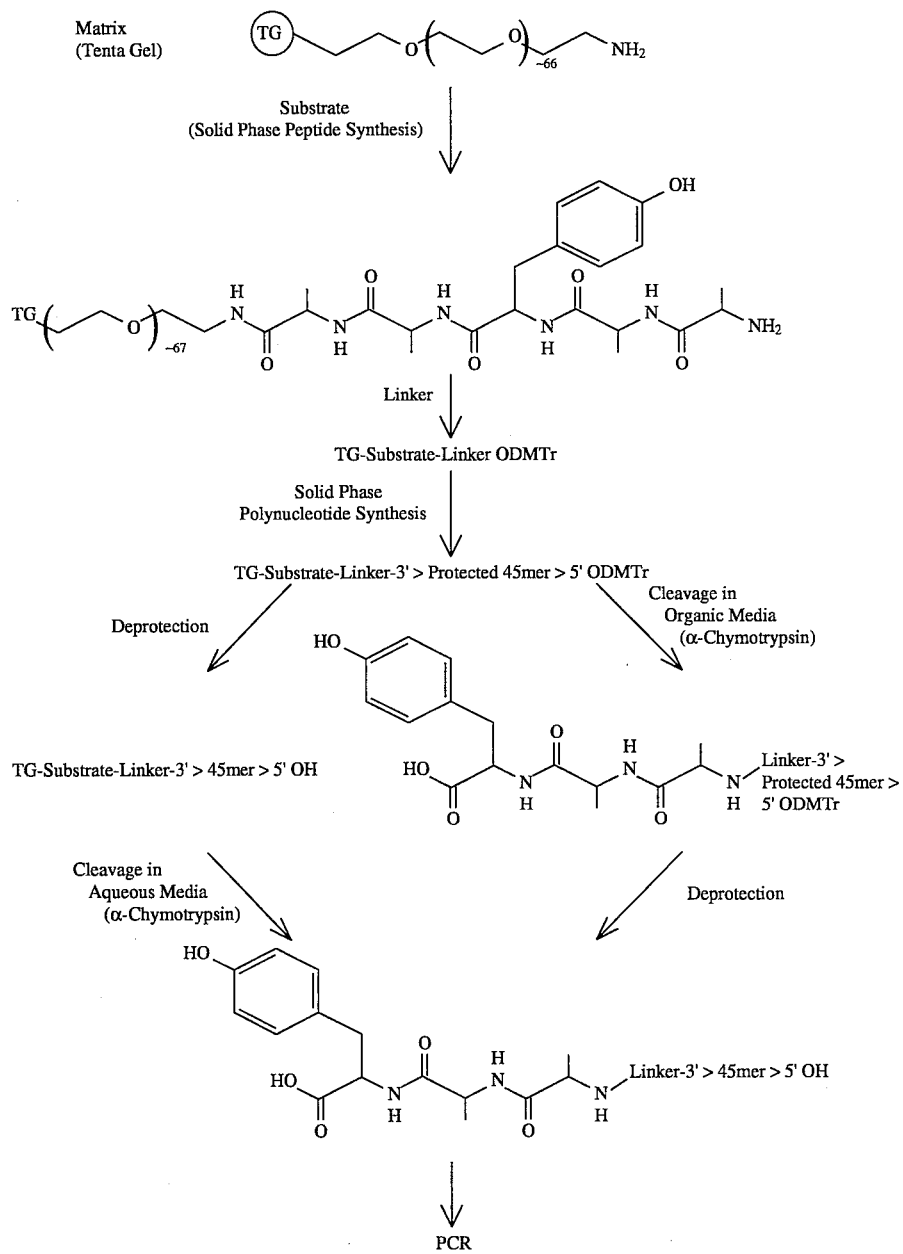

SCHEME 1

TentaGel is a tentacle copolymer of PEG (polyethylene glycol), and PS (polystyrene). It has been used successfully in solid phase peptide synthesis, e.g., B. G. de la Torre, B. G. et al. *Tetrahedron Lett.* (1994): vol. 35, pages 2733–2736; J. Haralambidis et al., *Tetrahedron Lett.* (1987): vol. 26, pages 5199–5202; and G. Barany, et al. in *Peptides: Pro-* ceedings of the Twelfth American Peptide Symposium (1992): Escon, Leiden, page 604. It has been used successfully in solid phase DNA synthesis, e.g., H. Gao et al. *Tetrahedron Lett.* (1991): vol. 32, pages 5477–5480 and P. Wright et al. *Tetrahedron Lett.* (1993): vol. 34, pages 3373–3376. TentaGel has also been shown to be compatible with biocatalysts, e.g., L., Meldal et al. *J. Chem. Soc., Chem. Commun.* (1994), p. 1849. It is stable to extremes of pH, and can be used in a variety of solvents. Its high swelling properties (4–7 times) in all usual solvents is an additional feature that makes it attractive for reactions involving biocatalysis. This polymer has the same mobility and dynamics as polyethylene glycol which has been used as a soluble support for oligonucleotide synthesis, e.g., E. Bayer, *Angew. Chem., Intl. Ed. Engl.* (1991): vol. 32, pages 5477–5480. It has a high diffusion coefficient, sorption, and mechanical stability. The reaction kinetics are of the same order as in solution because the functional groups are completely solvated (supra). Since the polyethylene glycol part of the resin (70–80% w/w), dominates its physico-chemical behavior the substrate-polynucleotide hybrid grown on it will be solubilized in organic or aqueous solutions. Finally, this matrix is commercially available with different functionalities (OH, $NH_2$, SH, $CO_2H$, CHO, Br), which will facilitate the introduction of different types of substrates.

Synthesis of the Substrate Portion of the Cassette. The catalyst chosen to study our cassette methodology had to be chemically and physically well defined. α-Chymotrypsin seemed to be an ideal enzyme for this purpose. The substrate portion of the cassette was L-Ala$_2$—L-Tyr—L-Ala$_2$ which is known to be the best substrate for α-chymotrypsin, e.g., W. K. Baumann et al., *Eur. J. Biochem.* (1973): vol. 39, 381–391. The choice of this substrate was dictated by the fact that our goal in these initial studies was to explore the lower limit of the sensitivity of the system.

It was not necessary to introduce a spacer between the solid support and the substrate since the TentaGel matrix is endowed with an extended polyethylene glycol arm bearing a terminal functional group that allows the direct attachment of the cassette substrate (Scheme 1). The loading of the matrix is about 280 millimoles/gram. In order to avoid the generation of hindered sites, we functionalized only the most exposed ones (40–60 millimoles/gram) by adding a large excess of matrix in the first step of the synthesis and capping the unreacted groups.

Figure 2:
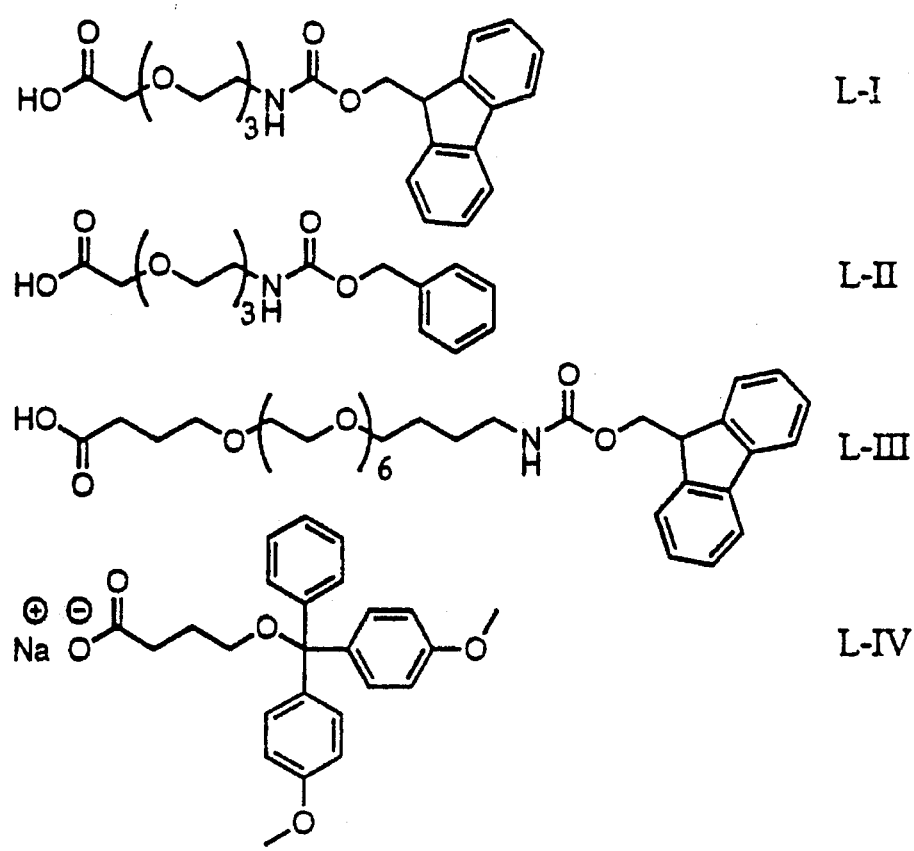
FIG. 2 illustrates the chemical structure of spacer units used in the construction of the cassettes.

We anticipated that the spacing between the substrate and the DNA tag was a critical design feature of the cassette and, thus, four different linkers were prepared (FIG. 2). Linker L-I looses slowly the Fmoc (9-fluorenylmethoxycarbonyl) protecting group inducing the formation of a side product that is not practical to separate from the pure compound. Thus, we prepared the more stable derivative L-II which has a CBZ (benzyloxycarbonyl) protecting group. Unfortunately, the acetoxy group in both L-I and L-II was found to be labile under the strongly acidic conditions required for the deprotection of the substrate ($CF_3CO_2H$/ethandithiol 95%, 2 hours). Accordingly, it is preferable to prepare a longer version of L-I, L-III which does not have the labile acetoxy moiety. However, L-III did not couple efficiently with peptide on the resin. Instead, the free amino group (matrix-peptide) reacted irreversibly with the Fmoc of the linker, e.g., G. B. Fields et al. *Int. J. Pep. Prot. Res.* (1990)L vol. 35, 161–214. Accordingly, these results teach that L-IV is the preferred linkage agent. All data reported herein employs cassettes with this linkage agent. Since only the above three linkage agents have been tested to date, there is a possibility that other as yet untested linker appendages may prove superior.

The peptide sequence selected as an exemplary substrate requires a deprotection step on the Tyrosine-O-t-Bu with $CF_3CO_2H$/ethandithiol, 95% for 2 hours. Since this deprotection can not be performed after the polynucleotide synthesis (concentrated acid leads to many side reactions on the polynucleotide), it was necessary to change the Tyrosine protecting group from a t-Bu to a base labile protecting group which can be removed at the same time as the deprotection of the DNA. Scheme 2 illustrates a pathway employed for protecting group exchange and for the introduction of the linker. Aside from its utility for the present experiment, this synthesis shows that the system can be readily transformed and modified chemically so as to be compatible with a variety of substrates.

SCHEME 2

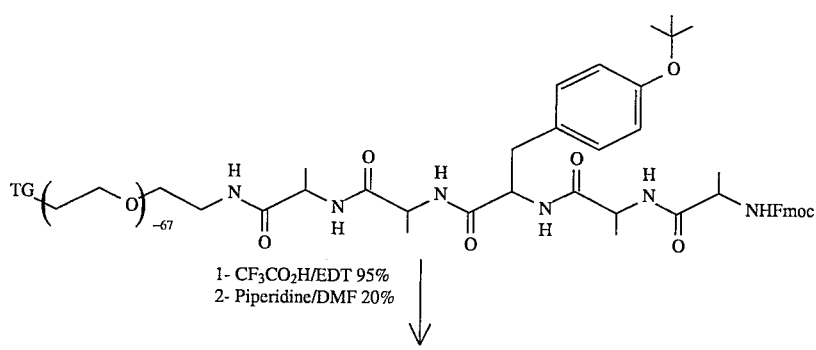

-continued
SCHEME 2

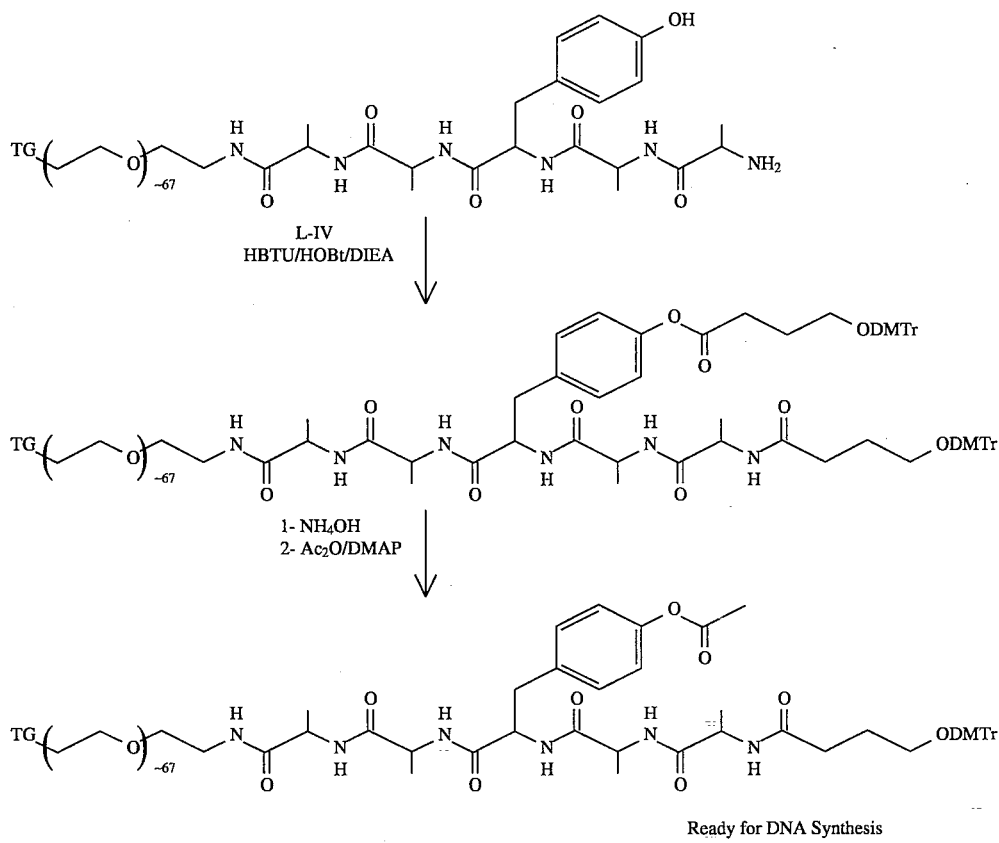

Ready for DNA Synthesis

Figure 3:
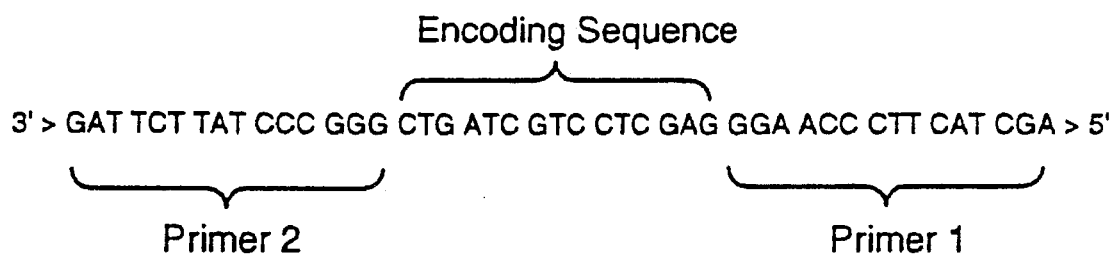
FIG. 3 illustrates a polynucleotide sequence (Seq. ID. No. 3) used for the substrate cassette.

Synthesis of the Polynucleotide Portion of the Cassette. The polynucleotide sequence is shown in FIG. 3. It possesses two primer sequences and one encoding sequence which identifies the substrate which in this case is a pentapeptide where each amino acid is arbitrarily assigned a triplet nucleotide sequence. Obviously, any nucleotide sequence may be used to encode the nature of the substrate and the choice of the nature of the code will depend primarily on the number and complexity of test substrates.

Standard phosphoramidite methodology using CPG solid support, on a 394 Applied Biosystem DNA Synthesizer, was not efficient with the TentaGel matrix, e.g. M. J. Gait, Ed. (1990) *Oligonucleotide Synthesis, a Practicable Approach* (Oxford University Press, New York). The yield per step dropped from ~98% to ~85%. After 45 steps, the overall yield with the CPG was ~40% and only ~0.07% with the TentaGel. Modification of the classical procedure was required. After many trials, three major modifications of the procedure (see materials and methods) were found to increase the yield per step from ~85% to ~97%, corresponding to an increase in the overall yield from ~0.07% to ~25%. The polynucleotide encoded peptide thus obtained was submitted to concentrated ammonia to deprotect the polynucleotide and the peptide, followed by 3% trichloroacetic acid in dichloromethane treatment to remove the dimethoxytrityl protecting group.

Figure 4:
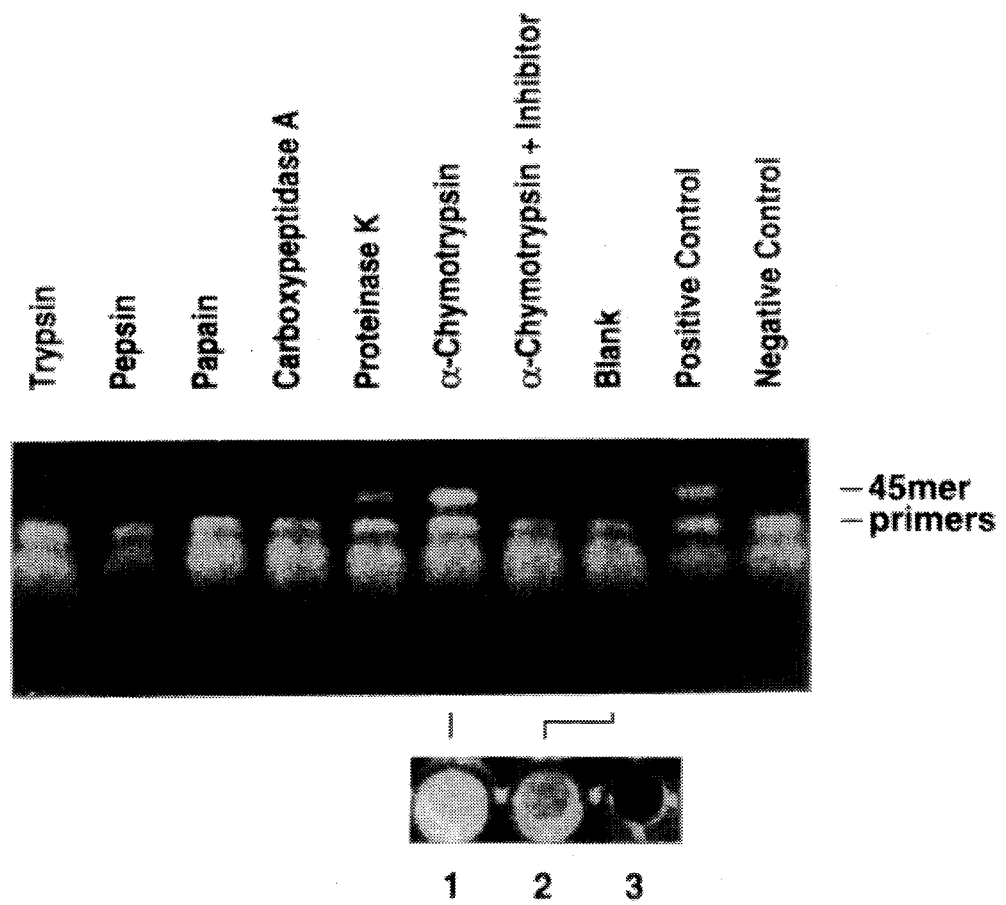
FIG. 4 illustrates the reaction specificity of a peptide reaction cassette with respect to several different proteolytic enzymes.

Reaction Specificity. The cassette was submitted to enzyme cleavage and the results after the amplification by PCR of the liberated polynucleotide are illustrated in FIG. 4.

Lanes 1–8 show the results after incubation at 20° C. for 30 minutes with trypsin, pepsin, papain, carboxypeptidase A, proteinase K, α-chymotrypsin, α-chymotrypsin+Bowman-Birk inhibitor, and no enzyme, e.g., Y. Birk, Y. *Int. J. Peptide Protein Res.* (1985): vol. 25, pages 113–131. Lane 9 corresponds to the positive control and lane 10 to the negative control.

The data in lane 6 show that in the presence of α-chymotrypsin a band corresponding to 45 nucleotides is present, indicating a net cleavage of the substrate by this enzyme. This interpretation is further supported by the control experiments. When the cassette is incubated with trypsin, pepsin, papain, or carboxypeptidase A, no band could be detected on the agarose gel which is in agreement with the specificity of these enzymes. When the Bowman-Birk inhibitor is added to α-chymotrypsin (lane 7), no cleavage is detected. As expected, in the presence of proteinase K a band is detected indicating a net cleavage by this enzyme. The intensity of the band indicates that the cleavage by proteinase K is weaker than that accomplished by α-chymotrypsin. This result is in agreement with the fact that α-chymotrypsin is specific for the substrate used in this study. In the absence of any enzyme (lane 8) no cleavage is detected after 30 minutes.

Under the reaction conditions used in this study, the enzymatic activity of 1 picomole of α-chymotrypsin was readily detected. One should be able to improve the sensitivity of detection since the substrate concentration (29.5 mM) used in our experiment was well below saturation (32). Additionally, preliminary experiments have shown that a longer linker between the substrate and the polynucleotide enhance the accessibility of the enzyme to the substrate (data not shown).

An alternative to analyzing the PCR products on agarose gel, which can become laborious when libraries of catalysts are being screened, one can simply add to the reaction mixture a fluorescent probe that undergoes fluorescence enhancement upon intercalation into the DNA. The insert in FIG. 4 shows a photograph taken under UV light (254 nm) of the reaction media in the presence of the YOYO-1. The first well corresponds to the experiment in lane 6, the second well to the experiment in lane 8, and the third to the probe in buffered solution without any additives. The greatest fluorescence enhancement is in the first well which contains the amplified DNA. The second well shows a background fluorescence resulting from the interaction of the probe with the primers. As expected, the third well does not show any detectable fluorescence. Another advantage of the YOYO-1 probe is that the amount of the PCR product (which should be directly related to the efficiency of the enzyme cleavage) can be quantified, e.g., M. Ogura et al., *Biotechniques* (1994): vol. 16, pages 1032–1033.

Reaction Sensitivity. It was interesting to note that after 24 hours, in the absence of α-chymotrypsin, a band corresponding to the DNA 45mer was detected (data not shown). This background reaction can be due to bond solvolysis anywhere between the solid support and the first bases of the polynucleotide, or simply to a leakage from the matrix. In an attempt to define the cleavage site(s) we prepared the same cassette lacking the substrate unit (where the polynucleotide is directly linked to the matrix via a mixed phosphodiester bond). When this matrix and the standard cassette are incubated separately without any catalyst, one can detect a background reaction after 16 hours. The ease of detection of this uncatalyzed reaction increases between 29 hours and 51 hours.

Figure 5:
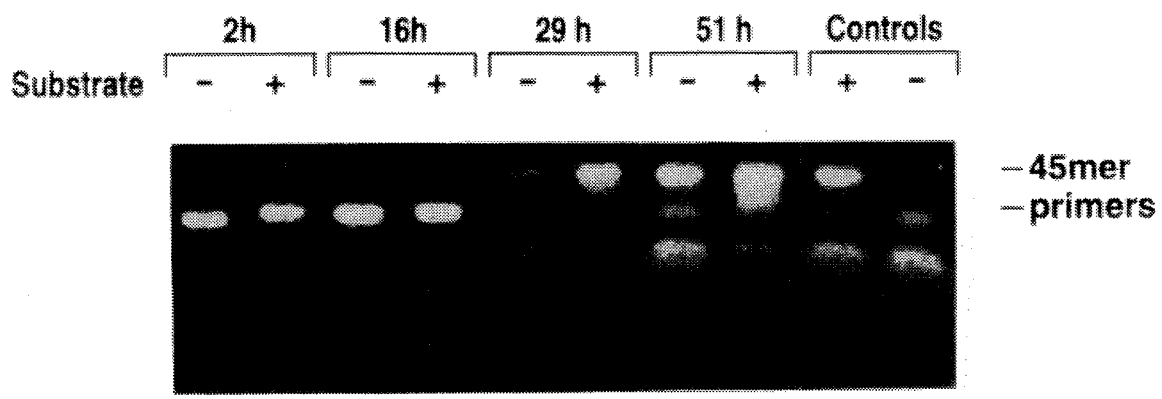
FIG. 5 illustrates the reaction sensitivity of the peptide reaction cassette of FIG. 4 as a function of time.

If this uncatalyzed reaction originated from leakage from the matrix or solvolysis of a phosphodiester bond, the 45mer DNA would have been detected at the same time irrespective of whether the cassette contained a substrate unit. The fact that detectable cleavage after 16 hours is limited to cassettes containing the peptide substrate indicates that bond solvolysis occurs in the substrate sequence, most likely at a peptide bond. After 16 hours when background cleavage of the peptide bond is observed, solvolysis of the phosphodiester bond is not detected, as indicated in FIG. 5. However, by 29 hours solvolysis of the phosphodiester bond is detected.

Assuming that the rate constant for a peptide bond hydrolysis is $\sim 3 \times 10^{-9}$ s$^{-1}$ ($t_{1/2} \sim 7$ years), at a cassette concentration of 29.5 mM the velocity for peptide bond hydrolysis is $\sim 9 \times 10^{-14}$ M/s, e.g., D. Kahn & W. C. Still, *J. Am. Chem. Soc.* (1988): vol. 110, pages 7529–7534. After 15 hours one would expect to have ~5 nanomoles of free polynucleotide in solution. This amount is known to be readily detectable by the PCR. Since the rate constant for phosphodiester bond hydrolysis is much slower ($5.7 \times 10^{-14}$ s$^{-1}$) than that of peptide bond hydrolysis, the background for the cassette lacking the substrate unit will be detected only after longer incubation times, e.g., E. H. Serpersu et al. *Biochemistry* (1987): vol. 26, pages 1289–1300.

Practicality of the Encoded Cassette System. It herein disclosed that the cassette system works reproducibly, and that the entire cassette can be assembled in less than 48 hours using conventional synthetic chemistry. Because of the simplicity and versatility of our methodology, analysis of a large number of potential catalysts can be carried out in less than 4 hours. Although, the current limit of detection is about ~1 picomoles, the sensitivity and efficiency of this system can be readily improved. These improvements may be achieved either by increasing the concentration of the substrate, and/or its loading on the solid support and/or introducing longer linkers between the substrate and the polynucleotide.

The system is not limited to transformations in which bond cleavage or bond formation is the initial event. The only requirement is that the chemical transformation make a bond labile to other reagents. For example, in the search for dihydroxylation catalysts, an olefin can be used as a substrate because when it is dihydroxylated it can be selectively cleaved by periodate. Additionally, one can envision systems in which the transformation modifies the cassette such that it now becomes a substrate for a known enzyme, e.g., K. Morikawa et al., *J. Am. Chem. Soc.* (1993): vol. 115, pages 8463–8464.

Finally, even using PCR conditions that are not yet optimized, it is herein demonstrated that one is able to detect in a matter of hours uncatalyzed chemical reactions with half-lives of years. This demonstrates that essentially any catalytic bond cleavage or formation event can in principle be readily detected in a very short time. The method should be applicable to detection of events that are of low efficiency either because the enzyme is poor or, more importantly, because the catalyst is only one member of a large library and is, thus, present in low concentration.

MATERIALS AND METHODS

The chemicals were purchased from Novabiochem and Aldrich for peptide synthesis, from Millipore for DNA synthesis, and from Promega for the PCR experiments. The YOYO-1 probe was purchased from Molecular Probes Inc. The solvents were purchased from Fisher or Baxter (water content <0.001%). For synthesis of the linkers, the chemicals were purchased from Aldrich, and were used without any further purification.

Substrate Synthesis. TentaGel is commercially available from Novabiochem or Rapp Polymere (Germany). The peptide was assembled according to standard Fmoc methodology, e.g., A. Aherton & R. C. Sheppard, *Solid Phase Peptide Synthesis: A Practicable Approach* (1989): Oxford University Press. In a typical procedure, 3 equivalents of the coupling reagent for amide bond formation, 2-(1H-Benzotriazole-1-yl)-1,1,3,3 tetramethyluronium Hexafluoro-phosphate (HBTU), 3 equivalents of N-Hydroxybenzotriazole (HOBt), 6 equivalents of N,N-diisopropyl-ethylamine (DIEA), and 3 equivalents of the N-a-(9-fluorenylmethoxy-cabonyl)-amino acid (Fmoc-aa) are added in dimethylacetamide to the resin swollen in dichloromethane (DCM). The coupling was completed in less than an hour as judged by the Kaiser test, e.g., E. Kaiser et al. *Analyt. Biochem.* (1970): vol. 34, page 595 and V. K. Sarin et al. *Analyt. Biochem.* (1981): vol. 117, 147. After each step the resin was washed with N,N-dimethyformamide, methanol, and DCM. The Fmoc protecting group was removed upon treatment with 20% piperidine in N,N-dimethylformamide (2×10 minutes). The yield of each step was determined by the titration of the Fmoc group from a small sample, e.g., A. Atherton, A. & R. C. Sheppard, R. C., *Solid Phase Peptide Synthesis: A Practicable Approach* (1989): Oxford University Press, p. 107. To have a final loading of 40–60 millimoles/gram, the first step of the synthesis was performed with four fold excess of solid support to Fmoc-aa. After all the final washings, the unreacted amino groups were capped (0.25 volume of acetic anhydride 4.23M in 2,6-lutidine; 0.75 volume of N,N-dimethylaminopyridine, 0.53M in THF, 2×10 minutes). The overall yield for peptide synthesis was ~98%.

The t-Butyl protecting group for the hydroxyl moiety on tyrosine was removed by treatment with $CF_3CO_2H$/ethandithiol 95% for 2 h, followed by extensive washing with DCM, methanol, and N,N-dimethylformamide. The Fmoc protecting group was removed before coupling to the linker (see scheme II). The matrix containing Tyrosine-O-L-IV was converted to Tyrosine-O-acetyl after selective deprotection of the phenolic ring (concentrated $NH_4OH$, 3 hours) and capping (0.25 volume of acetic anhydride, 4.23M in 2,6-lutidine, 0.75 volume of N,N-dimethylaminopyridine, 0.53M in THF, 30 min). The yield after each step was determined by the dimethoxytrityl cation assay, e.g., M. J. Gait, *Oligonucleotide Synthesis: A Practicable Approach* (1990): Oxford University Press, p. 48.

Linker L-IV was prepared in one step from the sodium salt of 4-hydroxybutyrate and dimethoxytrityl chloride in pyridine, e.g., H. Schaller et al., *J. Am. Chem. Soc.* (1963): vol. 85, pages 3821–3827.

DNA Synthesis. DNA synthesis was carried out on a 394 Applied Biosystem DNA Synthesizer. The standard 1 millimole cycle was modified as follows: 1) All washing steps 3, 59, 61, 66, 77, and 94 were prolonged to 30 seconds. The use of longer or shorter times decreased the yield. 2) The incubation time with phosphoramidite and tetrazole (step 45) was prolonged from 25 seconds to 120 seconds. 3) The concentration of the phosphoramidites was increased from 0.1M to 0.2M. The bases were deprotected upon treatment with concentrated $NH_4OH$ for 20 hours at 55° C. The dimethoxytrityl group is removed upon treatment with 3% trichloroacetic acid in DCM (5 minutes), followed by extensive washing with DCM, tetrahydrofuran, methanol, tris-HCl buffer (20 millimolar, pH 8, NaCl 160 millimolar), and $dH_2O$ (deionized water). After this step, the cassette is ready for use.

Enzymatic Cleavage and Inhibition Experiments. The cassette (1 mg, 5.9 millimoles/gram) was suspended in 20 ml tris-HCl buffer (20 millimolar, pH 8, NaCl 160 millimolar) and 170 ml $dH_2O$. 0.85 nmol of trypsin, pepsin, papain, carboxypeptidase A, α-chymotrypsin, or α-chymotrypsin+1 mg Bowman-Birk inhibitor (19) in 10 ml $dH_2O$ was added to the reaction media, and the mixture was shaken at 20° C. Supernatant fluids (18.7 ml) were taken after 30 minutes and were submitted to the PCR.

PCR Experiments. Aliquots (18.7 ml) from the reaction mixture were mixed with the PCR components ($MgCl_2$ 2.5 millimolar, 1.2 ml; Taq buffer, 2 ml; deoxynucleotide triphosphates 2.5 millimolar, 1.6 milliliters; primers 100 picomoles/milliliter, 1 milliliter). Taq polymerase(2.5 U, 0.5 ml), was added just before starting the first PCR cycle. A positive control (PCR components only) was run with $dH_2O$ containing 1 picomole of the polynucleotide sequence used in this study. A negative control was run under the same conditions without the polynucleotide sequence. The PCR was run on a Perkin-Elmer-Cetus 9600 instrument with the following cycle program: denaturation 94° C., 30 seconds; annealing 55° C., 30 seconds; extension 72° C., 30 seconds. After 35 cycles the results were analyzed on agarose gels (1% Gibco-BRL, 2% Nu Sieve GTG, TBE 1X, 103 millivolts).

Fluorescence Assay. After the PCR, the reaction supernatant (25 ml) was transferred to a 96-well ELISA plate and diluted to 250 ml with $dH_2O$ (175 ml) and methanol (50 ml). The probe (1 ml, YOYO-1) was added to this media, and the results were analyzed under UV light (254 nm).

Uncatalyzed Reactions. The cassette lacking the substrate unit was prepared as follows: TentaGel bearing a hydroxyl group functionality (1 g) was shaken with dimethoxytrityl chloride (10 eq, 85 mg) in pyridine (4 ml) at room temperature for 3 days. Titration of the dimethoxytrityl group showed a loading of 32 millimole/gram. The unreacted hydroxyl groups were acetylated (0.25 volume of acetic anhydride, 4.23M in 2,6-lutidine, 0.75 volume of N,N-dimethylaminopyridine, 0.53M in THF; 30 minutes). DNA synthesis was performed on this matrix following the procedure described above.

The cassette lacking the substrate (0.5 mg, 12.2 millimoles/gram) and the cassette with the substrate unit (1 mg, 6.2 millimoles/gram) were suspended separately in 20 ml of tris-HCl buffer (20 millimolar, pH 8, NaCl 160 millimolar) and 180 milliliter of $dH_2O$. The mixtures were shaken at 20° C. and aliquots (18.7 ml) taken after 2 hours, 16 hours, 29 hours, and 51 hours were subjected to the PCR.

What is claimed is:

1. An encoded reaction cassette for assaying a cleavage reaction comprising:
    a solid phase matrix;
    a substrate covalently linked to said solid phase matrix, said substrate being susceptible to cleavage by means of the cleavage reaction; and
    a first polynucleotide linked to said substrate, said first polynucleotide including a first PCR primer sequence, an encoding sequence, and a second PCR primer sequence, said encoding sequence positioned between said first and second PCR sequences.

2. An encoded reaction cassette as described in claim 1 further comprising:
    a first linker covalently linking said solid phase matrix to said substrate and
    a second linker covalently linking said substrate to said first polynucleotide.

3. An encoded reaction cassette as described in claim 1 wherein:
    said substrate is a polypeptide.

4. An encoded reaction cassette as described in claim 1 further comprising:
    a first linker covalently linking said solid phase matrix to said substrate,
    a second linker covalently linking said substrate to said first polynucleotide, and
    said substrate is a polypeptide.

5. An encoded reaction cassette as described in claim 1 further comprising:
    a second polynucleotide linked to said substrate, said second polynucleotide including the first PCR primer sequence, the encoding sequence, and the second PCR primer sequence.

6. An encoded reaction cassette as described in claim 2 further comprising:
    a third linker covalently linking said substrate to said second polynucleotide.

7. An encoded reaction cassette as described in claim 1 wherein: said substrate is a polypeptide having a suscepti-bility to proteolytic cleavage by a protease and said encoding sequence encodes the polypeptide.

8. An admixture of cleavage products from an encoded reaction cassette comprising:
    a solid phase cleavage product and
    a soluble phase cleavage product forming an admixture with said solid phase cleavage product,
    said solid phase cleavage product including a solid phase matrix and a first cleavage product of a substrate covalently linked to a solid phase matrix,
    said soluble phase cleavage product including a second cleavage product of the substrate covalently linked to a first polynucleotide, said first polynucleotide including a first PCR primer sequence, an encoding sequence, and a second PCR primer sequence, said encoding sequence separating said first and second PCR sequences.

9. An admixture of cleavage products from an encoded reaction cassette as described in claim 8 further comprising:
    said solid phase cleavage product including a first linker covalently linking said solid phase matrix to said first cleavage product and
    said soluble phase cleavage product including a second linker covalently linking said second cleavage product to said first polynucleotide.

10. An admixture of cleavage products from an encoded reaction cassette as described in claim 8 wherein:
    said first and second cleavage products are partial polypeptides.

11. An admixture of cleavage products from an encoded reaction cassette as described in claim 8 further comprising:
    said solid phase cleavage product including a first linker covalently linking said solid phase matrix to said first cleavage product,
    said soluble phase cleavage product including a second linker covalently linking said second cleavage product to said first polynucleotide, and
    said first and second cleavage products are fragments of a polypeptide.

12. An admixture of cleavage products from an encoded reaction cassette as described in claim 8 further comprising:
 a second polynucleotide linked to said second cleavage product of the substrate, said second polynucleotide including the first PCR primer sequence, the encoding sequence, and the second PCR primer sequence.

13. An admixture of cleavage products from an encoded reaction cassette as described in claim 8 further comprising:
 a third linker covalently linking said second cleavage product to said second polynucleotide.

* * * * *

UNITED STATES PATENT AND TRADEMARK OFFICE
CERTIFICATE OF CORRECTION

PATENT NO. : 5,559,000
DATED : September 24, 1996
INVENTOR(S) : Janda et al.

It is certified that error appears in the above-identified patent and that said Letters Patent is hereby corrected as shown below:

Column 1,
Line 4, under the heading "Statement of Government Rights", replace paragraph with the following:
-- This invention was made, in part, with government support under Grant Nos. GM 48351 and GM 43858 from the National Institutes of Health. The U.S. government may have certain rights in the invention. --

Signed and Sealed this

Twenty-sixth Day of March, 2002

Attest:

JAMES E. ROGAN
*Attesting Officer*  *Director of the United States Patent and Trademark Office*

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
( A ) LENGTH: 5 amino acids
( B ) TYPE: amino acid
( D ) TOPOLOGY: linear ( i i ) MOLECULE TYPE: peptide ( x i ) SEQUENCE DESCRIPTION: SEQ ID NO:1:

Ala  Ala  Tyr  Ala  Ala
1                     5

( 2 ) INFORMATION FOR SEQ ID NO:2:

( i ) SEQUENCE CHARACTERISTICS:
( A ) LENGTH: 5 amino acids
( B ) TYPE: amino acid
( D ) TOPOLOGY: linear (  i  i  ) MOLECULE TYPE: peptide (  i  x  ) FEATURE:
    ( A ) NAME/KEY: Modified-site
    ( B ) LOCATION: 3
    ( D ) OTHER INFORMATION: /label=Xaa
        / note="Xaa is Tyrosine-O-t-Butyl"

( x i ) SEQUENCE DESCRIPTION: SEQ ID NO:2:

Ala   Ala   Xaa   Ala   Ala
1                             5

( 2 ) INFORMATION FOR SEQ ID NO:3:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

GATTCTTATC  CCGGGCTGAT  CGTCCTCGAG  GGAACCCTTC  ATCGA          45